(12) United States Patent  
Larking et al.

(10) Patent No.: US 8,274,658 B2
(45) Date of Patent: Sep. 25, 2012

(54) OPTICAL MEASURING HEAD FOR A DUCT GAS MONITORING SYSTEM

(75) Inventors: Rikard Larking, Floda (SE); Peter Schachinger, Billdal (SE)

(73) Assignee: Siemens Aktiengesellschaft, München (DE)

(*) Notice: Subject to any disclaimer, the term of this patent is extended or adjusted under 35 U.S.C. 154(b) by 211 days.

(21) Appl. No.: 12/559,778

(22) Filed: Sep. 15, 2009

(65) Prior Publication Data

US 2010/0073679 A1   Mar. 25, 2010

(30) Foreign Application Priority Data

Sep. 24, 2008 (EP) ..................... 08016789

(51) Int. Cl.
*G01N 21/61* (2006.01)

(52) U.S. Cl. ........................................ 356/437
(58) Field of Classification Search ........... 356/437–439
See application file for complete search history.

(56) References Cited

U.S. PATENT DOCUMENTS

| | | | |
|---|---|---|---|
| 4,302,206 A * | 11/1981 | Profeta et al. ................. | 436/106 |
| 4,413,911 A | 11/1983 | Rice et al. | |
| 5,153,671 A * | 10/1992 | Miles ............................ | 356/301 |
| 6,071,375 A | 6/2000 | Chen et al. | |
| 7,319,524 B2 * | 1/2008 | Friedrichs .................... | 356/438 |
| 7,324,204 B2 * | 1/2008 | Kluczynski ................... | 356/437 |

FOREIGN PATENT DOCUMENTS

| | | |
|---|---|---|
| DE | 2701901 A1 | 7/1977 |
| DE | 2742972 A1 | 4/1979 |
| DE | 4315152 A1 | 11/1994 |
| EP | 1693665 A1 | 8/2006 |

* cited by examiner

Primary Examiner — Tara S Pajoohi Gomez

(57) ABSTRACT

An optical measuring head for a duct gas monitoring system is provided, the measuring head being mounted to an outer wall of a gas duct through which the duct gas flows. The measuring head has a longitudinal chamber which at one end opens into the gas duct and at the other end contains an active optical component. The chamber is flushed with a purge gas which, after flushing the chamber, is discharged into the gas duct. A gas line is installed between the chamber and interior of the gas duct at a point upstream of a discharge point and the purge gas is a branch-off of the duct gas.

7 Claims, 2 Drawing Sheets

OPTICAL MEASURING HEAD FOR A DUCT GAS MONITORING SYSTEM

CROSS REFERENCE TO RELATED APPLICATIONS

This application claims priority of European Patent Office Application No. 08016789.3 EP filed Sep. 24, 2008, which is incorporated by reference herein in its entirety.

FIELD OF INVENTION

The invention relates to an optical measuring head for a duct gas monitoring system, said measuring head being mounted to an outer wall of a gas duct through which the duct gas flows, said measuring head having a longitudinal chamber which at one end opens into the gas duct and at the other end contains an active optical component, said chamber being flushed with a purge gas which, after flushing the chamber, is discharged into the gas duct.

BACKGROUND OF INVENTION

Such an optical measuring head, which is known from EP 1 693 665 A1, contains a light source or an optical fiber end piece for sending a light beam through a measuring gas to a photodetector which is arranged in another such optical measuring head. The measuring heads are mounted at diametrically opposed locations to the wall of a gas duct through which the measuring gas flows. Each of the measuring heads has an optical window which separates a main chamber containing the respective active optical component (light source or photodetector) from a prechamber which opens to the gas duct. The main chambers and, if needed, the prechambers are flushed with a purge gas which is provided by a purge gas source. After flushing the main chambers, the purge gas is collected in a compensation cuvette to be irradiated by a compensation light beam. The portion of the purge gas which is fed into the prechambers is discharged into the gas duct. Though the purge gas should be free from the gas component to be measured, atmospheric gas components may leak into the purge gas and interfere with the measurement. Monitoring the collected purge gas in the compensation cuvette allows compensating any offset in the measurement caused by impurities in the purge gas.

From U.S. Pat. No. 6,071,375, a similar measuring head for monitoring optical emissions in a gas phase processing reactor is known where only the prechamber is flushed with a purge gas. The purge gas is provided by a purge gas source and delivered to the prechamber through a gas line. The purge gas may be an inert gas, such as helium, or may be a fraction of the process gas which is passed into the reactor through the prechamber. Preferably, a gas filter is provided in the gas line. The main chamber containing a detector system and a lens system remains unflushed.

SUMMARY OF INVENTION

In spectroscopic gas analysis, it is important that the gas component to be measured only appears in a defined measurement path, e.g. the gas duct (gas-leading pipe, furnace, funnel or the like). This is normally achieved by purging the optical components outside the measurement path with gas which does not contain the measured component. The costly drawback with this solution is that a lot of purging gas will be needed and that the purging gas needs to be well defined.

In order to overcome this drawback, the invention provides that, in the optical measuring head of the above-mentioned type, a gas line is installed between the chamber and the interior of the gas duct at a point upstream of the discharge point and that the purge gas is a branch-off of the duct gas.

Using the duct gas as the purge gas makes the chamber, which contains the active optical component, part of the measurement path. The pressure drop generated by the duct gas flow in the gas duct causes the diverted purge gas to flow through the chamber.

If there is no optical window in the chamber, the discharge point is at the one end of the chamber where it opens into the gas duct.

If the chamber contains an optical window dividing the chamber into a main chamber containing the active optical component and a prechamber, a further gas line is installed between the main chamber and the interior of the gas duct at a point downstream of the one end of the prechamber where it opens into the gas duct. To purge the process side of the window, a branch line may branch off from the gas line to the prechamber.

If the main chamber contains a lens system dividing the main chamber into two sections, a connecting pipe is installed between the two sections to allow the purge gas to flow from the one to the other section.

If the pressure drop between the points of withdrawal and return of the purge gas is too low for independently driving the purge gas through the chamber, a pump may be provided in the gas line or the further gas line.

Further, a gas filter may be provided in the gas line to retain particles from the duct gas passing through it.

BRIEF DESCRIPTION OF THE DRAWINGS

The present invention will be now described, by way of example, with reference to the accompanying drawings, in which.

DETAILED DESCRIPTION OF INVENTION

Figure 1:
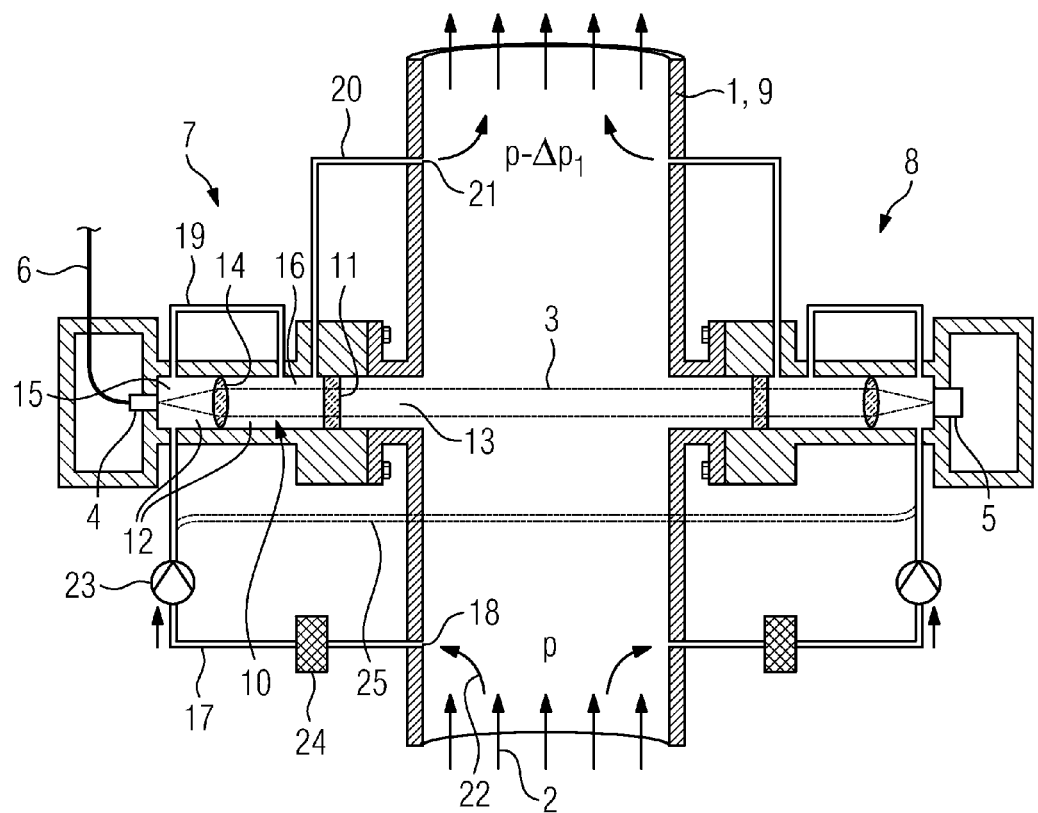
FIG. 1 is a cross sectional view of a diode laser gas analyzer comprising two optical measuring heads arranged on opposite sides of a gas duct.

FIG. 1 shows a gas duct 1 through which a duct gas 2 flows. The flow direction is indicated by the arrows. To measure the concentration of selected gas components, laser light 3 is sent from a light transmitting active optical component 4 through the gas duct 1 to a light receiving active optical component 5. The light transmitting active optical component 4 may be a laser diode or the end piece of an optical fiber 6 which carries the light of an external light source. The light receiving active optical component 5 may be any conventional kind of photodetector. The active optical components 4 and 5 are arranged in respective different optical measuring heads 7 and 8 which are mounted at diametrically opposed locations to the wall 9 of the gas duct 1. Each of the measuring heads 7 and 8, which are largely identical in construction (as far as the measuring heads 7 and 8 are identical, duplicate reference numerals are omitted for the sake of simplicity), has a longitudinal chamber 10 which at one end opens into the gas duct 1 and at the other end contains the respective active optical component 4 or 5. In the shown example, the chamber 10 contains an optical window 11 dividing the chamber 10 into a main chamber 12 containing the active optical component 4 or 5 and a prechamber 13 which is open the gas duct 1. The main chamber 12 contains a lens system 14 dividing the main chamber 11 into two sections 15 and 16.

A gas line 17 leads from the interior of the gas duct 1 at a point 18 upstream of the mounting position of the measuring head 7 (or 8) to the first section 15 of the main chamber 12. A connecting pipe 19 connects the first section 15 to the second section 16 from which a further gas line 20 leads to the interior of the gas duct 1 at a point 21 downstream of the mounting position of the measuring head 7 (or 8).

Driven by the pressure drop $\Delta p_1$ in the gas duct 1 between the point 18 and 21, a minor portion of the duct gas 2, which serves as a purge gas 22, is diverted into the gas line 17 at point 18, fed through the sections 15 and 16 of the main chamber 12 and afterwards via the further gas line 20 returned into the gas duct 1. If the pressure drop $\Delta p$ proves to bee to low, a pump 23 may be provided in the gas line 17 or the further gas line 20. Further, a gas filter 24 may be provided in the gas line 17 to retain particles, such as sooth, from the duct gas 2 passing through it. As indicated by numeral 25, the purge gas 22 for both measuring heads 7 and 8 may be withdrawn at a single point 18 so that the measuring head 8 does not need its own pump or filter.

Figure 2:
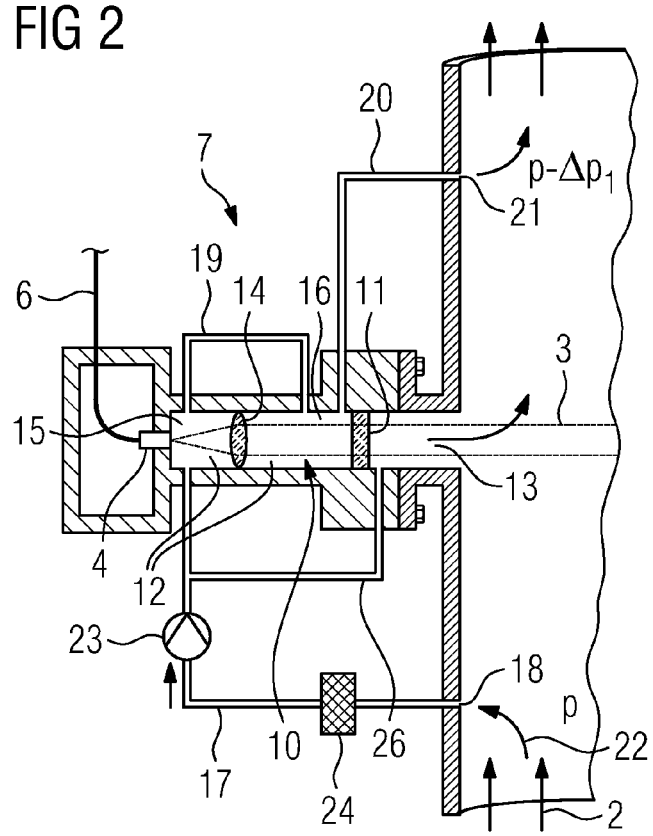
FIG. 2 shows a variant embodiment of one of the optical measuring heads.

FIG. 2 shows a variant embodiment of the optical measuring head 7 where a branch line 26 branches off from the gas line 17 to the prechamber 13 for purging the process side of the window 11.

Figure 3:
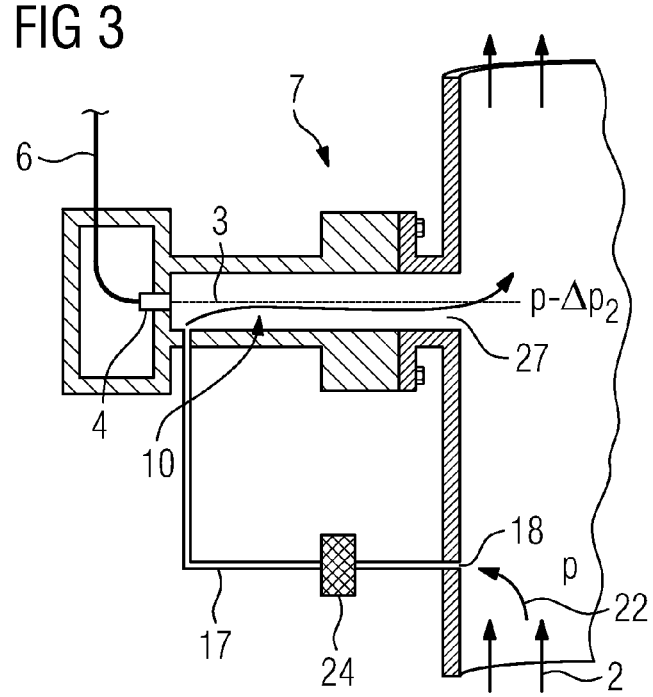
FIG. 3 is another variant embodiment of the optical measuring head.

In the other variant embodiment shown in FIG. 3, the chamber 10 does not contain any lens system or window so that the discharge point 27 is at the one end of the chamber 10 where it opens into the gas duct 1.

The invention claimed is:

1. An optical measuring head for a duct gas monitoring system, the measuring head being mounted to an outer wall of a gas duct through which the duct gas flows, comprising:

a longitudinal chamber which, at a first end, opens into the gas duct and, at a second end, contains an active optical component, wherein the chamber is flushed with a purge gas which, after flushing the chamber, is discharged directly into the gas duct, wherein a gas line is installed between a first section of the chamber, defined in part by the second end, and an interior of the gas duct at a point upstream of a discharge point, wherein the discharge point is at the first end of the chamber which opens into the gas duct, and wherein the purge gas is a branch-off from the duct gas.

2. The optical measuring head of claim 1, wherein the chamber contains an optical window dividing the chamber into a main chamber containing the active optical component and a prechamber, and wherein a further gas line is installed between the main chamber and interior of the gas duct at a point downstream of one end of the prechamber, the one end opening into the gas duct.

3. The optical measuring head of claim 2, wherein a branch line branches off from the gas line to the prechamber.

4. The optical measuring head of claim 3, wherein the main chamber contains a lens system dividing the main chamber into two sections, a connecting pipe being installed between the two sections.

5. The optical measuring head of claim 2, wherein the main chamber contains a lens system dividing the main chamber into two sections, a connecting pipe being installed between the two sections.

6. The optical measuring head of claim 2, wherein a pump is provided in the gas line or the further gas line.

7. The optical measuring head of claim 1, wherein a gas filter is provided in the gas line.

* * * * *